(12) United States Patent
Chiodo

(10) Patent No.: US 8,578,889 B2
(45) Date of Patent: Nov. 12, 2013

(54) SPECIMEN ALIGNMENT AND HEAD HOLDING SYSTEM FOR IMAGING MACHINES

(71) Applicant: Chris D. Chiodo, Warren, MI (US)

(72) Inventor: Chris D. Chiodo, Warren, MI (US)

( * ) Notice: Subject to any disclaimer, the term of this patent is extended or adjusted under 35 U.S.C. 154(b) by 0 days.

(21) Appl. No.: 13/649,815

(22) Filed: Oct. 11, 2012

(65) Prior Publication Data

US 2013/0061812 A1  Mar. 14, 2013

Related U.S. Application Data

(62) Division of application No. 12/079,890, filed on Mar. 31, 2008, now Pat. No. 8,322,310.

(51) Int. Cl.
*A01K 1/03* (2006.01)
(52) U.S. Cl.
USPC .......................................... 119/420
(58) Field of Classification Search
USPC ......... 119/751, 416, 417–421, 712, 752, 755, 119/756
See application file for complete search history.

(56) References Cited

U.S. PATENT DOCUMENTS

| | | | | |
|---|---|---|---|---|
| 4,332,244 A | * | 6/1982 | Levy et al. | 128/205.25 |
| 4,941,431 A | * | 7/1990 | Anderson et al. | 119/420 |
| 6,711,430 B1 | * | 3/2004 | Ferris et al. | 600/417 |
| 7,146,936 B2 | * | 12/2006 | Dazai et al. | 119/756 |
| 7,414,403 B2 | * | 8/2008 | Chiodo | 324/321 |
| 7,806,082 B2 | * | 10/2010 | Nelson | 119/420 |
| 2001/0053878 A1 | * | 12/2001 | Ferris et al. | 600/415 |
| 2004/0216737 A1 | * | 11/2004 | Anderson et al. | 128/203.12 |
| 2008/0047554 A1 | * | 2/2008 | Roy et al. | 128/203.15 |
| 2008/0072836 A1 | * | 3/2008 | Chiodo | 119/417 |
| 2008/0168951 A1 | * | 7/2008 | Starr et al. | 119/751 |
| 2009/0000567 A1 | * | 1/2009 | Hadjioannou et al. | 119/755 |
| 2011/0071388 A1 | * | 3/2011 | Yared et al. | 600/425 |

* cited by examiner

*Primary Examiner* — Monica Williams
*Assistant Examiner* — Joshua Huson
(74) *Attorney, Agent, or Firm* — Lawrence J. Shurupoff

(57) ABSTRACT

A laboratory specimen, such as a mouse or rat, can be accurately and repeatedly imaged in an imaging machine, such as an MRI machine, when securely positioned on a specimen support bed. The support bed includes contours and accessories for centering a specimen on the support bed. One or more bite bars coact with a head clamp to accurately fix a specimen's head in the same position time after time.

19 Claims, 17 Drawing Sheets

US 8,578,889 B2

SPECIMEN ALIGNMENT AND HEAD HOLDING SYSTEM FOR IMAGING MACHINES

This application is a divisional of U.S. patent application Ser. No. 12/079,890, filed Mar. 21, 2008, which is incorporated herein in its entirety.

GOVERNMENT RIGHTS

This invention was made with government support under contracts 1 R41 NS050141-01 and 3 R41 NS050141-0151 awarded by the National Institutes of Health (NIH). The government has certain rights in the invention.

BACKGROUND OF THE INVENTION

1. Field of the Invention

The present invention relates in general to apparatus for holding a specimen, such as a laboratory animal, in a fixed position during an imaging procedure such as X-ray, CAT, and CT scans and MRI and PET imaging. The invention relates in particular to such apparatus which provide for the accurate repeatable positioning of a specimen time and again within the same imaging machine or within a number of different imaging machines.

2. Description of Prior Developments

Medical researchers and other investigators often use laboratory animals such as rats, mice and other rodents in the course of various studies and investigations. Such studies sometimes require the use of imaging machines to produce a series of images of one or more anatomical features of the specimen over a period of time. Images of the brain, heart and other organs as well as musculoskeletal features are commonly repeatedly imaged over a period of time.

In order to take accurate, repeatable images of the same area of the specimen, the specimen must be held tightly in the same position relative to the imaging apparatus. In the past, a pair of retention bars or retention screws was snugly inserted within a rodent's ears for holding the rodent in a relatively fixed position during imaging.

A problem can arise with the use of conventional ear bars when a specimen must be imaged within a small, tight enclosure, such as within a small diameter bore of a small imaging coil in an MRI machine. Small bore imaging coils are desirable for imaging small specimens such as laboratory rodents because, in general, the smaller the bore of the imaging coil, the better is the clarity of an image.

As conventional ear bars or ear screws extend laterally or radially outwardly when placed within the bore of an imaging coil, they can limit the use of conventional specimen holders to larger bore imaging coils, and larger imaging machines with larger imaging areas. Moreover, relatively large conventional ear bars can interfere with the placement of small gradient coils around the head area of a specimen.

SUMMARY OF THE INVENTION

The present invention has been developed to eliminate the need for conventional laterally-projecting ear bars so as to allow for accurate, repeatable imaging of a laboratory specimen within small, tight imaging spaces, such as within small diameter bores of MRI imaging coils. In particular, the present invention is directed to an animal holder which sets, references and positions an animal within a holder using a contoured body alignment bed and hard rigid contact and abutment against the animal's front incisor teeth and optionally against the animal's rear molar teeth. A resilient yoke or adjustable clamp can also be used to bear against the sides of the specimen's head or within a specimen's ears to provide further alignment and positioning of the specimen on an alignment bed.

A front incisor bite bar fixes the position of the animal's front incisor teeth to provide a first axial and radial reference point, and one or more rear molar supports such as a rear bite bar can fix the animal's rear molar teeth in a predetermined plane defined by the front and rear pair of bite bars. In this manner, the specimen can be repeatedly imaged in the same relative position time and again, over the course of study.

In accordance with one embodiment of the invention, a specimen is repeatably positioned and held in a desired stereotaxic alignment within an animal holder. The body, legs, and tail of a specimen are fitted closely within alignment guides such as recesses and grooves matching the shape of the specimen. One or more incisor bite bars or rails can work in combination with an optional molar bite bar or rail for engaging hard bone-like components and teeth in the mouth of the specimen. These hard points of contact establish spatial reference points for properly and accurately positioning a specimen in all three dimensions of space.

These positive hard points of contact within a specimen's mouth in no way interfere with any surrounding imaging components or machinery. Moreover, these hard points of contact can provide a more accurate and repeatable positioning of specimens as compared to prior systems which relied at least in part on contact with soft tissue, such as ear tissue, to position and restrain a specimen.

In one embodiment, the two front teeth of a rodent can be hooked over a front incisor bar or tooth rail to provide a fixed rigid point of reference. At the same time, one or more molar bite bars or rails are forced in a wedge-like manner against the bottom of the specimen's upper molars or rear teeth. This wedges and locks the head of the specimen in a preferred and repeatable position. The use of the spaced-apart bite bars and molar rails in hard abutting contact with the specimen's teeth aligns the specimen's head in a fixed plane passing through the contact surfaces of the bite bars and molar rails.

A wedge or head clamp, which can be incorporated in an anesthesia gas scavenging hood, can be used to press against the specimen's head and thereby force the specimen's teeth into contact with the front incisor bite bar and rear molar rail. The clamp or hood can be formed as a half-ring or half-cone which can be moved axially or longitudinally with respect to the specimen's head so as to wedge downwardly on the specimen's nose and/or head and rearwardly towards the specimen's tail to repeatably fix the specimen in a predetermined spatial orientation. The arched or inverted V-shaped inner contour of the half-ring head clamp hood provides a centering and wedging action which drives a specimen's head into a predetermined laterally-centered and axially-fixed position on the animal holder.

Anesthesia gas can be delivered directly into the specimen's nose and mouth through a compact ported gas delivery block and then exhausted through the removable and adjustable gas scavenging head clamp hood. In one embodiment, a cross bar can be mounted on the clamp hood to contact the bridge of the specimen's nose and wedge it downwardly so that contact is made against the incisor bar and molar rail. This ensures contact with only hard body parts, i.e., teeth.

In one embodiment, the incisor bar and molar rails can be constructed as an integral one-piece unit which can be mounted to a slideway for axial adjustment to accommodate specimens of different sizes. In another embodiment, one or more laterally-spaced longitudinally-extending molar rails can extend upwardly from the bite bar and into the specimen's mouth at a small angle, such as about 3 degrees. This aligns the specimen's head at a predetermined stereotaxic imaging angle in all axial positions.

The head clamp can also be adjustably arranged on a slideway to be driven axially, either manually by a push or pull, or mechanically by a screw drive, back and forth into and out of engagement with a specimen. The head clamp, incisor bar and molar rails can be mounted to an end block which can be mounted on a vertical or inclined slideway for even further adjustment of the position of the rodent's head into a preferred standard imaging position, previously determined solely by ear bars. This provides repeatable specimen positioning and imaging in three dimensions. A proper or desired set point of the rodent's head can be indicated by laser beams or other indicating means such as mechanical pointers.

An alternate or supplement to the molar rail or rails is a registration plate which fits between the rodent's molars and presses upwardly against the rodent's palate. Although a rodent's palate typically has some soft tissue, this tissue is typically a very thin covering over hard bone or cartilage. Accuracy of placement using a rodent's palate can be close to that achieved with molar rails.

In one embodiment, the incisor bar, molar rail or rails and/or registration plate, as well as the head clamp and compact anesthesia gas delivery and exhaust system can be mounted on a live specimen alignment bed which is contoured to accurately position a specimen along three axes, time and again within a small bore imaging machine. The specimen alignment bed can be mounted to an animal holding system, which can be connected to a specimen positioning system. The specimen positioning system can be mounted to a positioning assembly system adapted to be mounted to an imaging machine.

Additional accessories can be used in combination with the present invention, including radio-frequency coils, such as inert surface coils, for improving imaging quality and fluid delivery systems for providing conditioning air to a specimen, such as warm air, or warm water. Warming fluid helps to stabilize a specimen exposed to cryogenic cooling fluid which surrounds the superconducting magnetic coils within which a specimen may be placed. Additional fluid delivery systems can be provided to deliver and exhaust anesthesia gasses to a specimen.

The aforementioned objects, features and advantages of the invention will in part, be pointed out with particularity, and will, in part, become clear from the following more detailed description of the invention, taken in conjunction with the accompanying drawings, which form an integral part thereof.

DETAILED DESCRIPTION OF THE PREFERRED EMBODIMENTS

Figure 1:
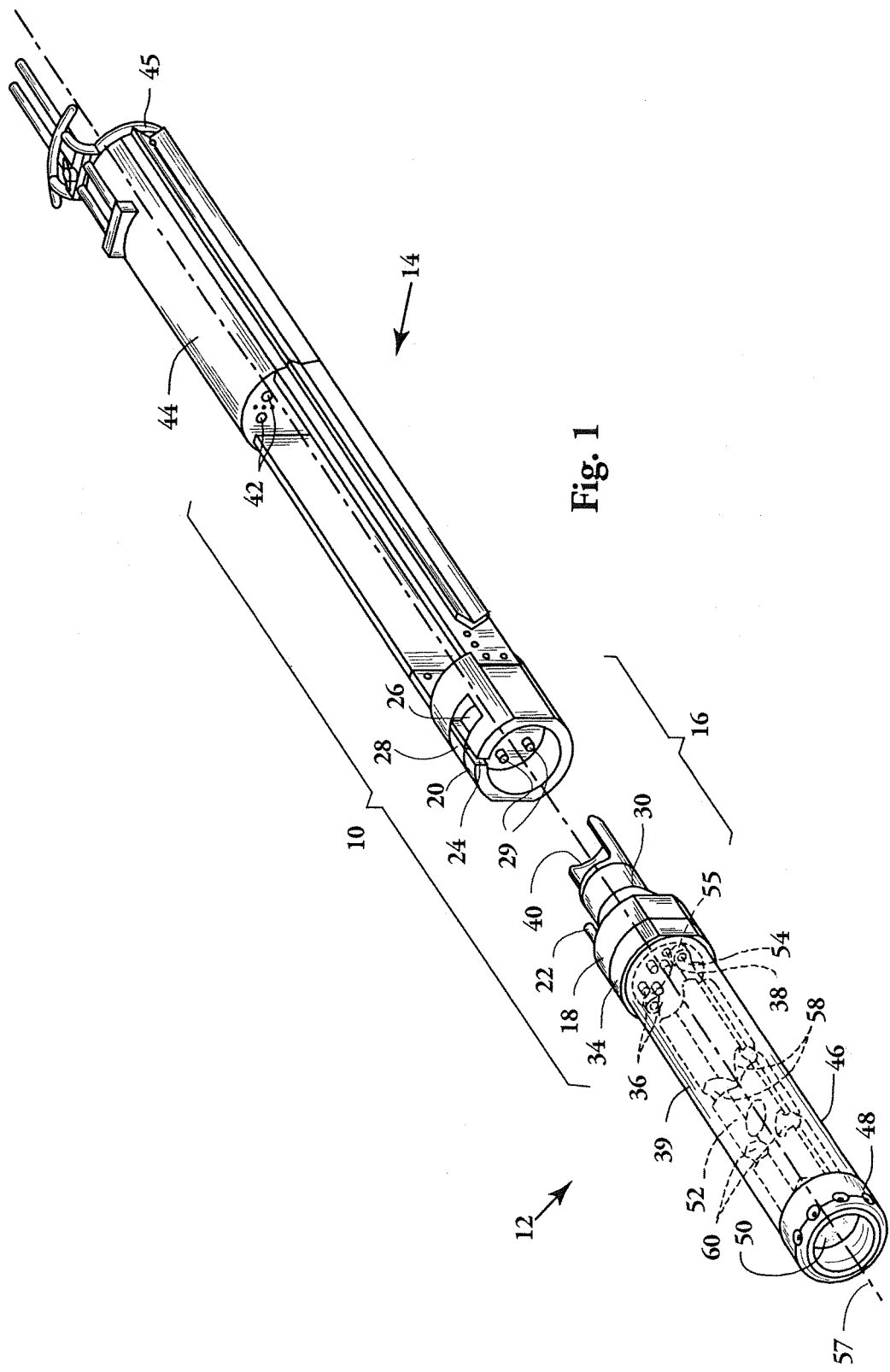
FIG. 1 is a perspective exploded view of one example of an animal management system, also called a specimen positioning system, adapted for use in an MRI machine and showing a specimen alignment system in dashed lines mounted within a tubular animal holding system.

A first embodiment of the present invention will now be described in conjunction with the drawings, beginning with FIG. 1 which shows an animal management system or specimen positioning system 10 representative of one system within which the alignment and head holding apparatus may be used. The positioning system 10 is adapted for use in an MRI positioning assembly such as disclosed in US patent application publication number US 2005/0027190A1, filed Aug. 10, 2001, under application Ser. No. 10/631,226, entitled Positioning Assembly for Magnet Coils and Specimens, and which is incorporated herein in its entirety by reference.

The positioning system 10 is also adapted for use in a modular system of the type disclosed in U.S. patent application Ser. No. 11/346,850 filed Feb. 3, 2006, entitled Specimen Positioning System for Imaging Machines, and which is incorporated herein in its entirety by reference. The positioning system 10 shown in FIG. 1 includes a detachable modular specimen holder or animal holding system 12, which is removably and selectively mountable on a positioning receiver assembly 14, which is adapted for mounting on an imaging machine.

A modular coupling 16 is provided between the animal holding system 12 and the positioning receiver assembly 14 for accurately and repeatably coupling the animal holding system 12 to the positioning receiver assembly 14 to form a specimen positioning system 10. Coupling 16 includes a male coupling portion 18 mounted on an outer end or rear end of the animal holding system 12 and a female coupling portion 20 mounted on an inner or front end of the positioning receiver assembly 14.

Once the male coupling portion 18 is inserted within the female coupling portion 20, a male keying member 22 projecting from a predetermined circumferential or clockwise position (such as 12 o'clock) on the male coupling portion 18 is inserted and guided into a complementary keying slot 24 formed at a predetermined circumferential or clockwise position (such as 12 o'clock) in or on the female coupling portion 20 so as to circumferentially align the animal holding system 12 with the positioning receiver assembly 14. This clockwise alignment ensures proper, accurate and repeatable placement of a specimen held within the animal holding system 12 within a known, generally horizontal, axial plane within the field of an imaging machine.

In order to lock or to release and separate the male coupling portion 18 to or from the female coupling portion 20, an operator need only rotate or push a cam tab 28 in opposite directions. When released, the animal holding system 12 can then be easily removed and placed in another positioning receiver assembly 14 in a different type of imaging machine. Additional details of the quick-connect and quick-disconnect coupling 16 are provided in U.S. patent application Ser. No. 11/346,851, filed Feb. 3, 2006, entitled Coupling Assembly for Animal Management Systems, the entirety of which is incorporated herein by reference.

As further shown in FIG. 1, the animal holding system 12 further includes an interconnection panel 34 which includes various ports and fluid connectors 36 for the passage of fluids, such as anesthesia gasses, heating and/or cooling fluids and various electrical connectors 38 for the connection of sensor lead wires from ECG sensors and respiratory sensors, for example, located within a cylindrical animal holding chamber 39. The fluid ports 36 and electrical connectors 38 communicate with aligned passages formed through the male coupling portion 18 to which the panel 34 is connected.

A lead support tray or trough 40 receives and supports the electrical wires and fluid tubes exiting the outer end of the male coupling portion 18. These wires and tubes extend from within the panel 34, through channels or passages through the male coupling portion 18 and outwardly through passages 29 along the positioning receiver assembly 14. They then pass through one or more conduits 42 formed through the cylindrical base 44 of the positioning receiver assembly 14. The tubes and electrical leads can then be respectively connected to external sources of fluids and to remote monitoring devices via an outer connector plate 45 which includes fluid and electrical connectors for quick and easy connection and disconnection with the external monitoring devices.

The specimen or animal chamber 39 includes a cylindrical tube 46 removably connected and hermetically sealed to the interconnection panel 34. Tube 46 may be made of clear or transparent plastic or glass. An end cap 48 can be threaded onto an inner threaded open end of tube 46 as shown in FIG. 1. A porous filter 50 can be clamped or mounted to the inner end of tube 46 by end cap 48.

In order to accurately position and restrain a specimen, such as a laboratory rat, within the animal holding system 12, a live specimen alignment bed 52 is accurately positioned axially and circumferentially (clockwise) within tube 39.

Figure 2:
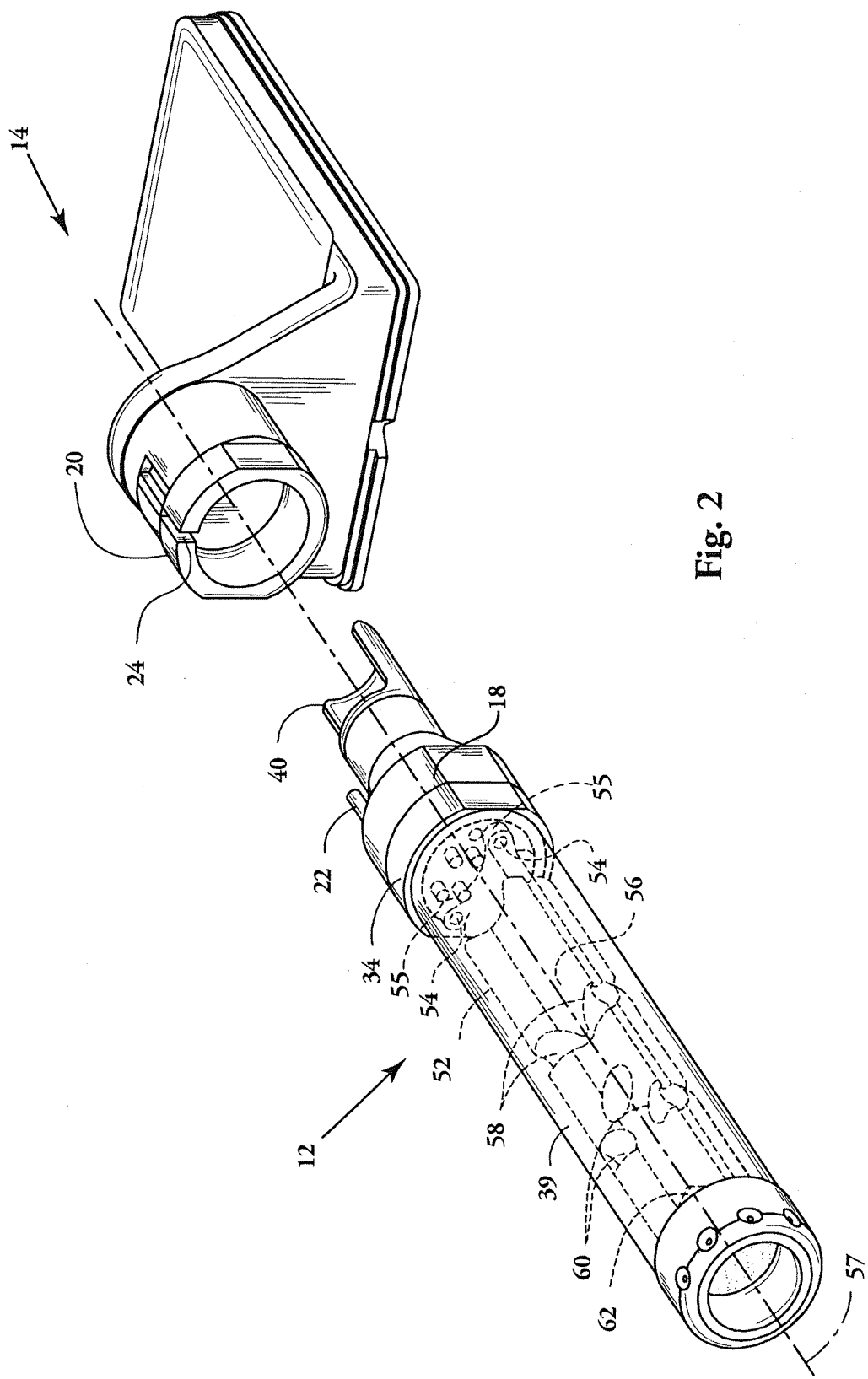
FIG. 2 is a perspective exploded view of an animal management system adapted for use in a CT or PET imaging machine and showing a specimen alignment system in dashed lines.

A different type of specimen holder is disclosed in U.S. patent application Ser. No. 11/526,115, filed Sep. 22, 2006, having the same inventor as the present invention. The outer end of the alignment bed 52 is accurately and removably mounted to and cantilevered from the interconnection panel 34 by a pair of apertured flanges 55 having eyelets 54 (FIG. 2) which align with threaded bores in the interconnection panel 34. Threaded fasteners such as plastic screws can be used to fix the alignment bed 52 to the interconnection panel 34 via eyelets 54. Additional keying and alignment may be provided between the alignment bed 52 and the interconnection panel 34 using, for example, axially-extending keying pins and sockets, wherein the pins nest closely within the sockets.

Figure 3:
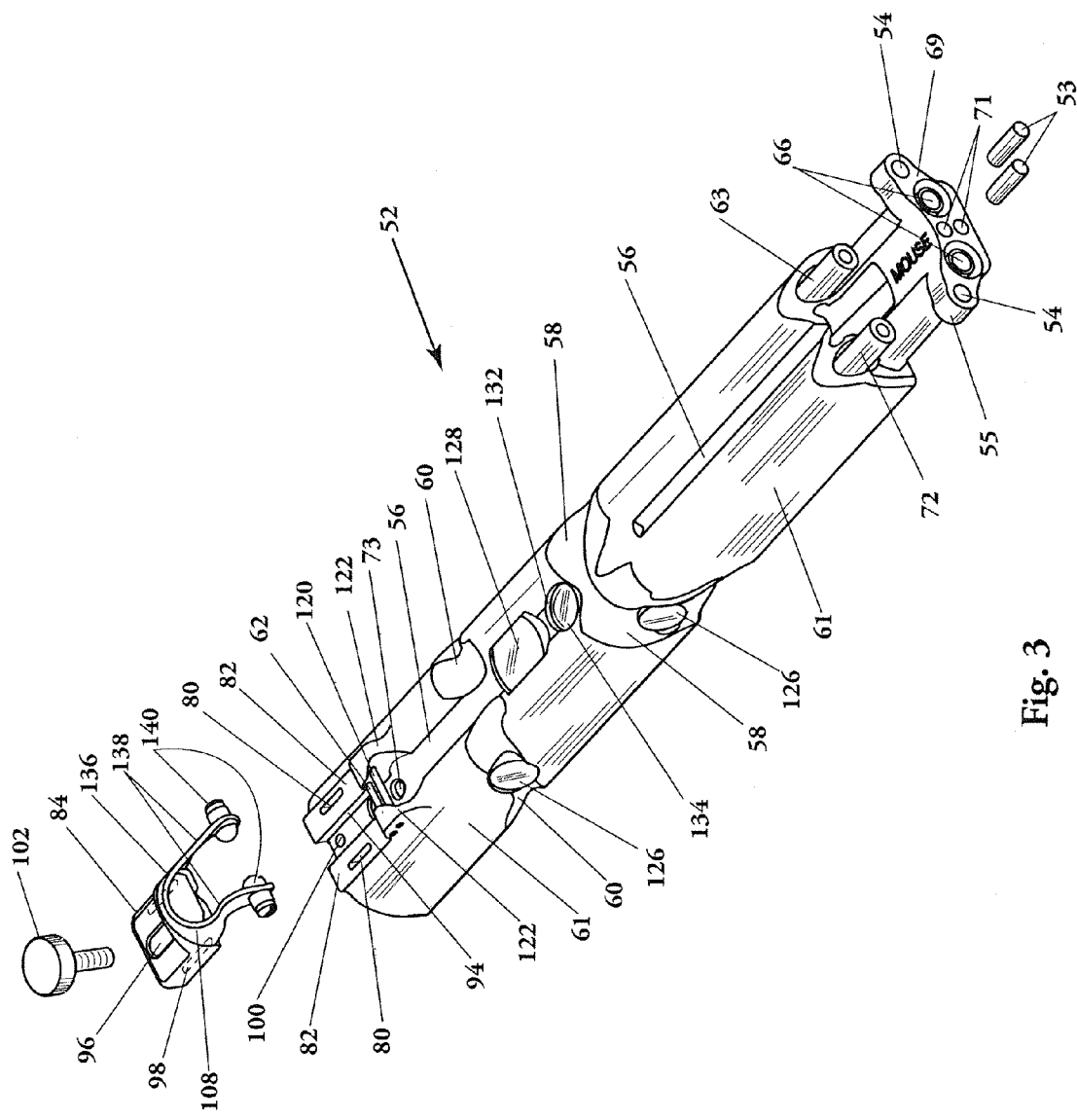
FIG. 3 is an exploded perspective view of a first embodiment of an animal alignment system embodied as an animal alignment bed constructed in accordance with the present invention.

As seen in FIG. 3, the alignment bed 52 is formed with a central longitudinal groove or channel 56 for accurately aligning and holding the body and tail of an animal centrally within the tube 39. Channel 56 extends closely parallel with the central axis 57 (FIG. 1) of tube 39 to align the spine and tail of an animal, such as a rodent, parallel with axis 57. Rearwardly and downwardly extending rear grooves or rear leg channels or slots 58 are formed in and beneath bed side portions or bed sidewalls 61. The rear leg channels 58 extend longitudinally or axially rearwardly along alignment bed 52 for positioning and fixing in predetermined place the rear legs of an animal. Forwardly and downwardly-extending grooves or leg channels or slots 60 are likewise formed in the sidewalls 61 of alignment bed 52 for positioning and fixing in predetermined place the front legs of an animal. This arrangement of forwardly and rearwardly extending leg grooves mimics and corresponds to the position of a rodent lying on a pipe or tree branch, and seems to provide a comfortable, natural prone positioning for a resting rodent.

An advantage of having sidewalls 61 extending downwardly from channel 56 is the ability to fully support a specimen's legs on three sides within leg grooves 58 and 60. That is, the front, rear and inner surfaces of a specimen's legs are naturally constrained and accurately positioned in a comfortable manner within the leg grooves 58 and 60 so as to protect the specimen's legs during handling, mounting and imaging.

A front incisor bite bar 62 (FIG. 3) is placed at the inner or front end portion of the alignment bed 52 serve as a registration surface and to anchor an animal's front or incisor teeth 115 (FIG. 17) in a known axial (longitudinal) position which corresponds to a position closely adjacent to the centerline or "sweet spot" of the field of view of each imaging machine into which the positioning system 10 (FIG. 1) is subsequently mounted. A head clamp 84 (FIG. 3) may also be provided to center and lock an animal's head in a predetermined axial location, a predetermined lateral or transverse location and a predetermined radial or circumferential orientation on the alignment bed 52.

Figure 4:
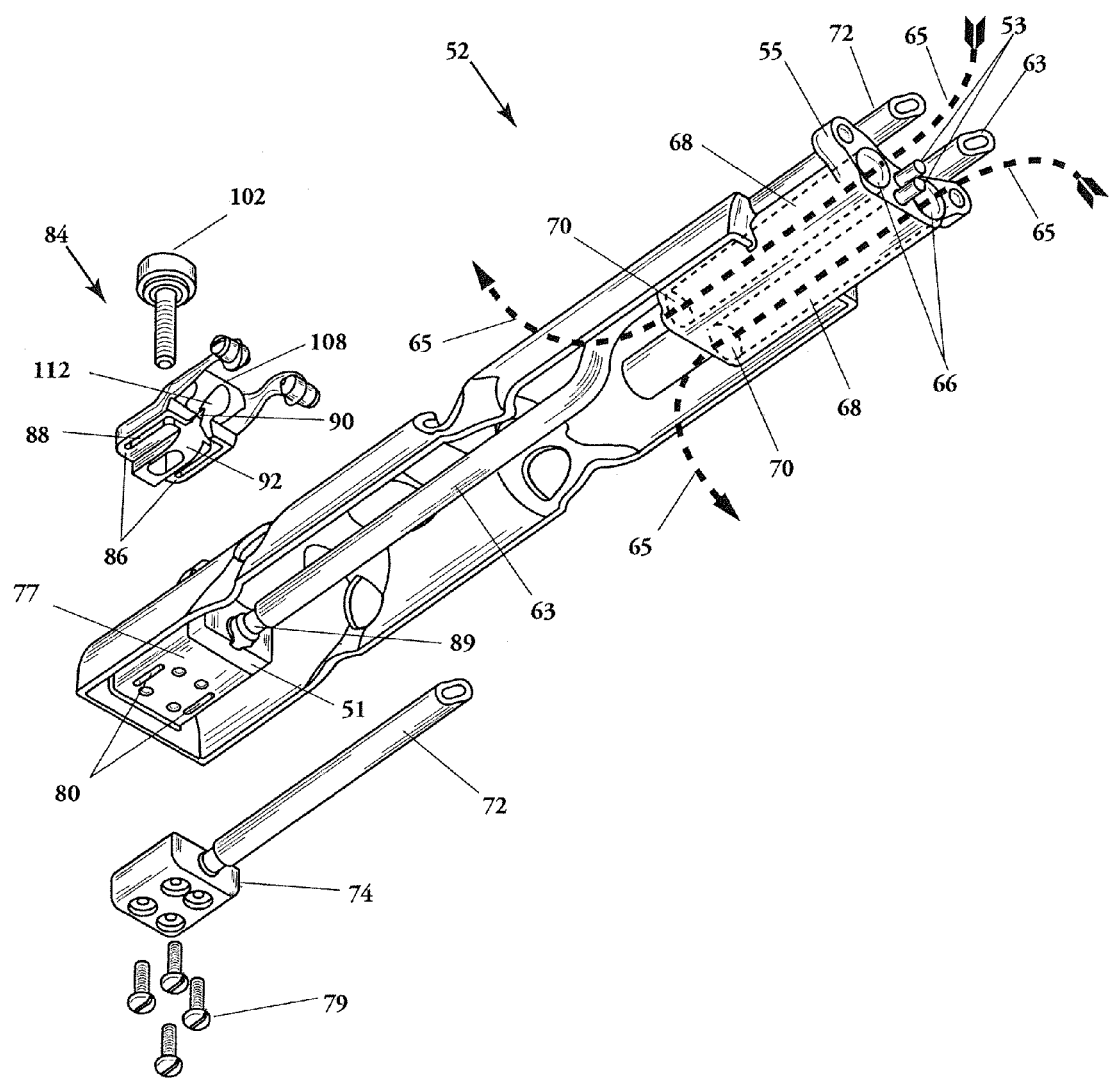
FIG. 4 is a bottom perspective view of FIG. 3.
Figure 5:
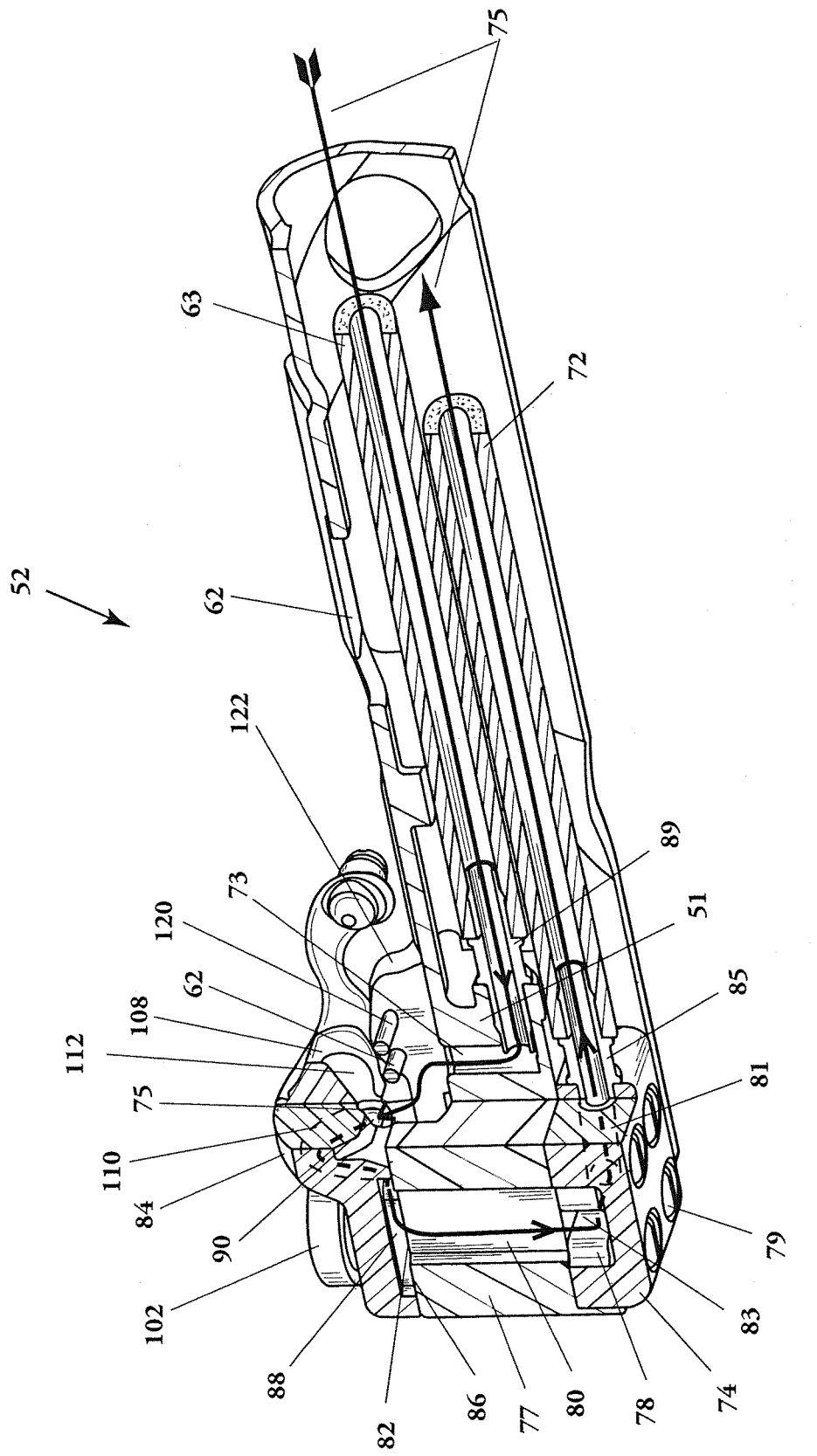
FIG. 5 is a partial view in section of the alignment system of FIG. 3 showing the flow of fluid through the system.

Additional details of one embodiment of an alignment bed 52 are further shown in FIGS. 3, 4 and 5. As seen in FIGS. 3 and 4, the specimen alignment platform or support bed 52 is formed, for example, by plastic molding as a lightweight thin-walled hollow beam. Other manufacturing techniques include carbon fiber lay-up using carbon sheets and epoxy resin placed on a form, and stereo lithography sintering (SLS). Bed 52 is adapted to be cantilevered from interconnection panel 34 (FIG. 1) by eyelets 54 on mounting flanges 55 through which fasteners may be threaded into panel 34 to anchor the rear wall 69 of bed 52 against the panel 34. Additional support can be provided to the forward end of the support bed 52 as described further below in connection with FIGS. 15 and 16.

When the bed 52 is tightly mounted to panel 34, fluid intake ports 66 on rear end wall 69 are aligned with fluid outlet ports on panel 34 for receiving fluids such as warm air or warm water for warming a specimen during imaging procedures. For additional precision in locating the bed 52 on panel 34, axial bores 71 (FIG. 3) are positioned to receive dowel pins 53 (FIG. 4) extending axially from the interconnection panel 34.

As seen in FIG. 4, any fluid or gas 65 entering intake ports 66 flows longitudinally through axial flow channels 68 and exits the channels 68 via exhaust ports 70. The gas exiting ports 70 then flows throughout the holding chamber 39 (FIG. 1) to warm or otherwise condition or treat a specimen positioned on bed 52.

As further shown in FIGS. 3 and 4, anesthesia gas or other fluid may be delivered to the mouth and nose area of a specimen restrained on the alignment bed 52 via a combination anesthesia hood and head clamp 84. In one example, a flexible plastic hose 63 can be connected at one end to a fitting or nipple 36 on panel 34 for receiving anesthesia gas. As seen in FIG. 5, the other end of the plastic hose 63 can be connected to a fitting 89 on or near an intake port 73 formed in a ported block portion 51 provided on the front end of the alignment bed 52. As represented by the directional arrows 75 in FIG. 5, anesthesia gas is channeled upwardly through intake port 73 into the mouth and nose region of a specimen, adjacent to the front bite bar 62.

After anesthesia gas flows over the mouth and nose of a specimen, it is exhausted through the combination exhaust hood and head clamp 84 and out through the panel 34 (FIG. 1) through an exhaust line. As seen in FIGS. 3 and 5, a flexible plastic anesthesia gas exhaust hose or exhaust tube 72 extends from the rear end portion of the alignment bed 52 to the front end portion of the alignment bed 52. The flexible plastic exhaust tube 72 can be fitted over a nipple exhaust fitting on a fluid or gas exhaust outlet port on panel 34 (FIG. 1).

Figure 6:
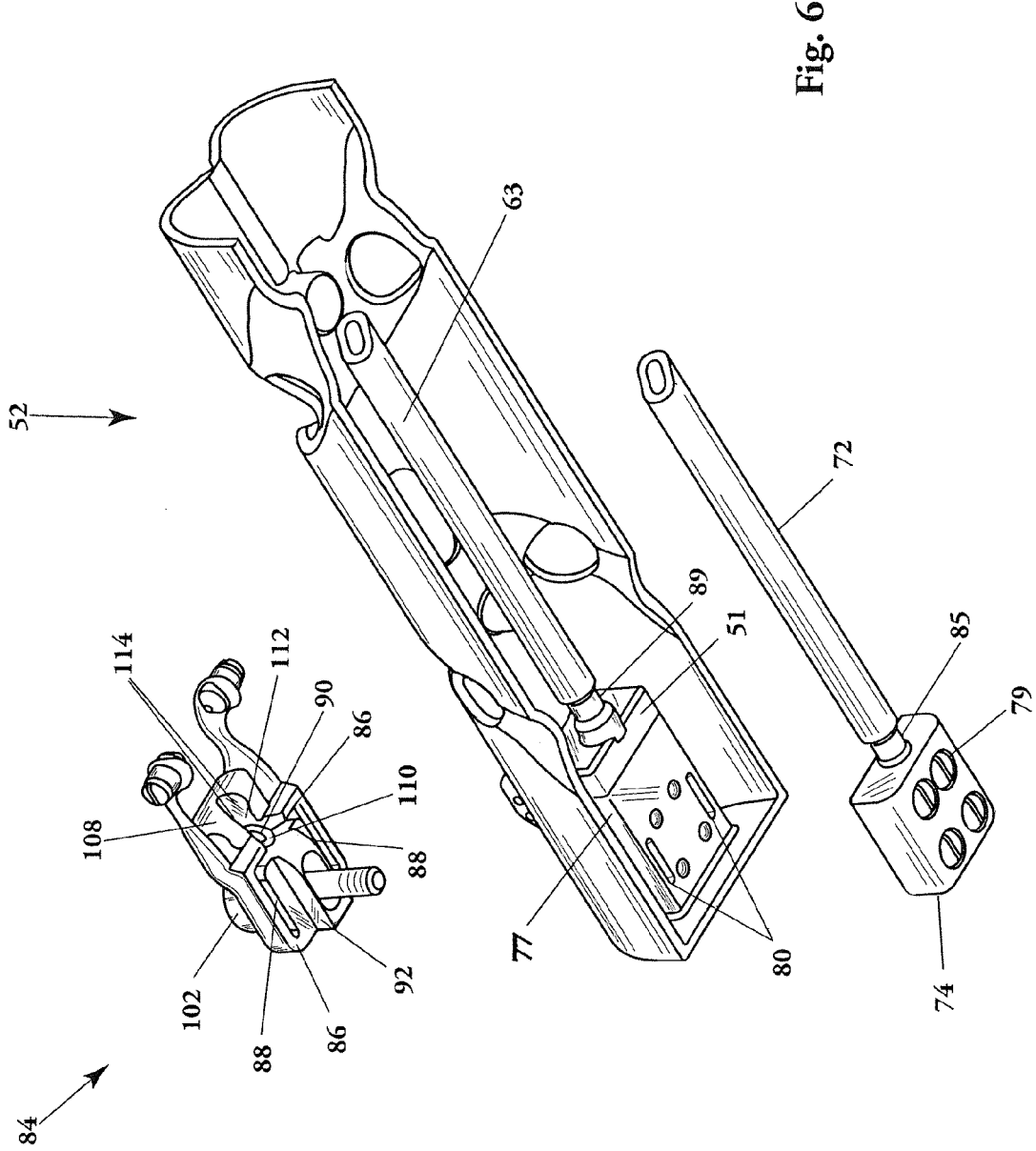
FIG. 6 is a partial bottom exploded perspective view showing a hood and clamp member adapted for use with the alignment system of FIG. 3.
Figure 7:
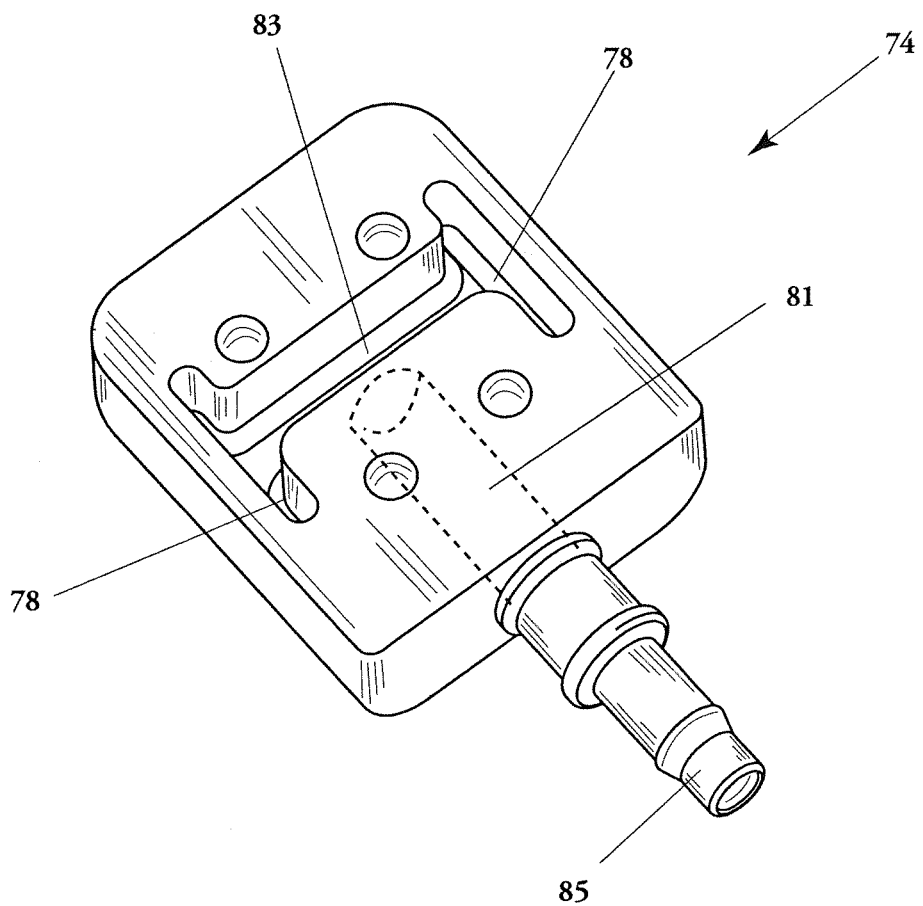
FIG. 7 is a perspective view of a ported manifold block for exhausting gas from the alignment system of FIGS. 3 and 4.

As seen in FIGS. 5, 6, and 7, a ported manifold block 74 is attached to a ported exhaust manifold block 77 molded integrally on the front end portion of the alignment bed 52. Exhaust manifold block 77 may also be provided as a separate cast or machined plastic component and fixed to the alignment bed with plastic screws or adhesives. The manifold block 74 has an exhaust bore or channel 81 (FIG. 5) which communicates with exhaust hose 72 via fitting 85. The manifold blocks 74 and 77 can be formed as a single cast or machined component if desired, and formed with a single flow path or multiple flow paths therethrough.

Channel 81 also communicates with a common exhaust collection chamber 83 (FIG. 7). Chamber 83 divides into a pair of distribution exhaust channels 78 which remove gas from the gas hood and clamp member 84. The channels 78 respectively communicate with a pair of upwardly-extending elongated slots 80 (FIGS. 5 and 6). Slots 80 (FIG. 3) exit the top surface of bed 52 through a pair of flat manifold pads 82.

While hoses 63 and 72 can in some embodiments extend all the way to a point adjacent the front bite bar 62, these hoses can become relatively bulky and obtrusive when connected to very narrow alignment beds 52. As higher resolution images are possible with smaller bore imaging machines, it is desirable to make the beds 52 as narrow as possible. This is achieved by forming the narrow flow paths for intake and exhaust gas through ported blocks 51, 74 and 77. These flowpaths can be machined or molded with very small profiles thereby minimizing the bed size and separating and spacing the gas hoses 63, 72 away from the crowded end portion of the support bed.

As seen in FIGS. 4 and 6, the hood and clamp member 84 has a bottom portion foamed with a pair of flat sliding pads 86 adapted to slide over the manifold pads 82. An elongated slot 88 is formed through each sliding pad 86. Slots 88 are positioned to align over and communicate with slots 80 over a predetermined length of longitudinal or axial travel.

Each slot 88 extends through the hood and clamp member 84 and joins together and communicates with a common fluid exhaust port 90. Fluid, such as anesthesia gas, can be efficiently exhausted from the arched recessed area around a specimen's nose and mouth through an exhaust flow path extending along bed 52. This flowpath extends via port 90 in the gas hood and clamp member 84, from the front to the rear of bed 52 through the exhaust manifold block 77, manifold block 74, block 51 exhaust hose 72 and couplings 18 and 20 and through the positioning receiver assembly 14 to an external gas collection or recirculation apparatus (not shown).

An elongated tongue 92 (FIG. 6) extends downwardly between the sliding pads 86 on the hood and clamp member 84 to fit closely within an axially-extending groove 94 (FIG. 3) formed between the manifold pads 82 on alignment bed 52. This tongue-and-groove sliding interconnection centers the hood and clamp member 84 on the front end of the alignment bed 52.

As seen in FIGS. 3 and 5, the hood and clamp member 84 is longitudinally or axially adjustable along, and closely retained within, groove 94 by the tongue and groove interconnection. An axially-extending slot 96 (FIG. 3) is formed through a front portion 98 on the hood and clamp member 84. A threaded bore 100 (FIG. 3) is formed through the front end portion of the alignment bed 52 for receiving a set screw 102 passing through the slot 96 on the hood and clamp member 84.

Figure 9:
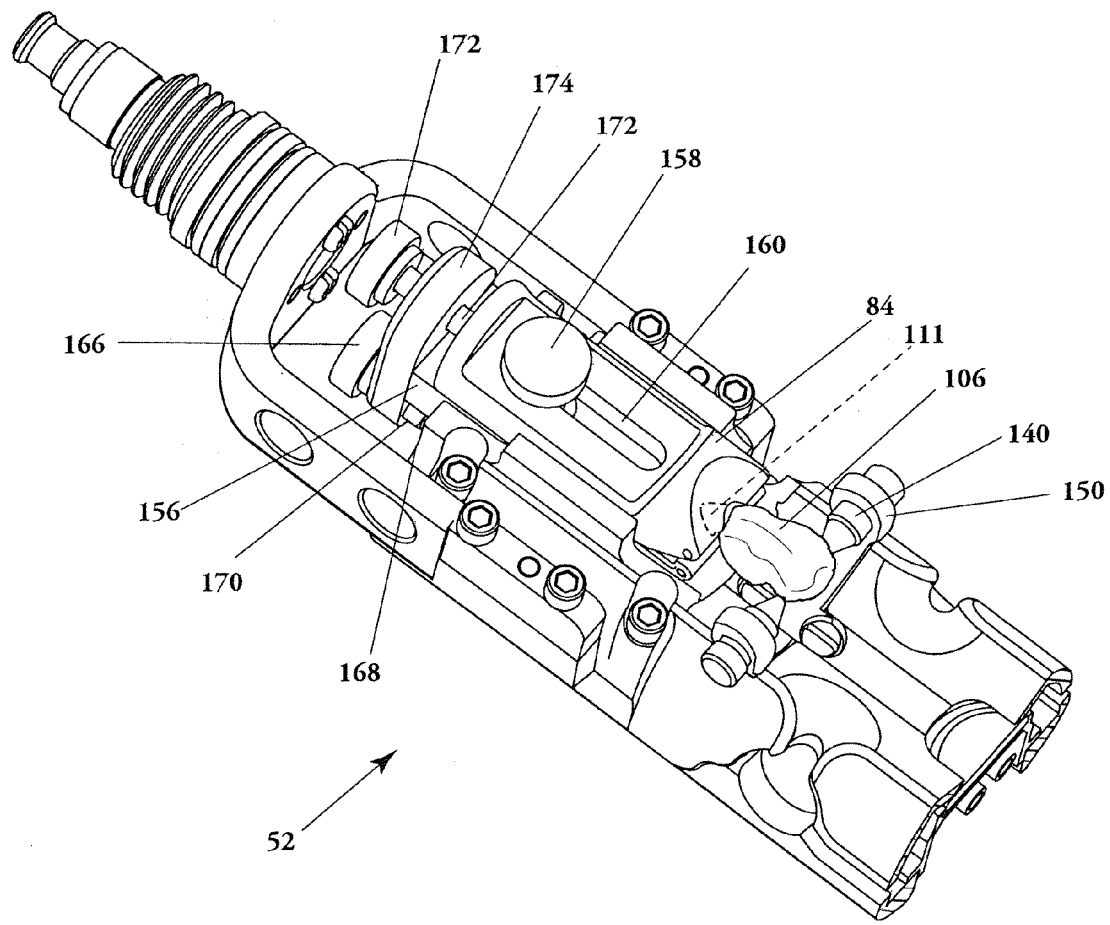
FIG. 9 is a partial perspective view of the front end portion of the alignment system and specimen holder of FIG. 8 showing the placement of a rodent's skull within the bite bar and clamping assembly.

Set screw 102 passes freely through slot 96 in the hood and clamp member 84 and threads into bore 100. By loosening set screw 102, the head and clamp member 84 can be easily slid axially over the manifold pads 82 toward and away from a specimen's head 106 (FIG. 9). Once the head and clamp member 84 is adjusted into a desired position, it can be locked in place by tightening the set screw 102 to clamp and fix the head and clamp member 84 tightly to the manifold pads 82 so as to form a gas-tight seal therebetween.

Figure 17:
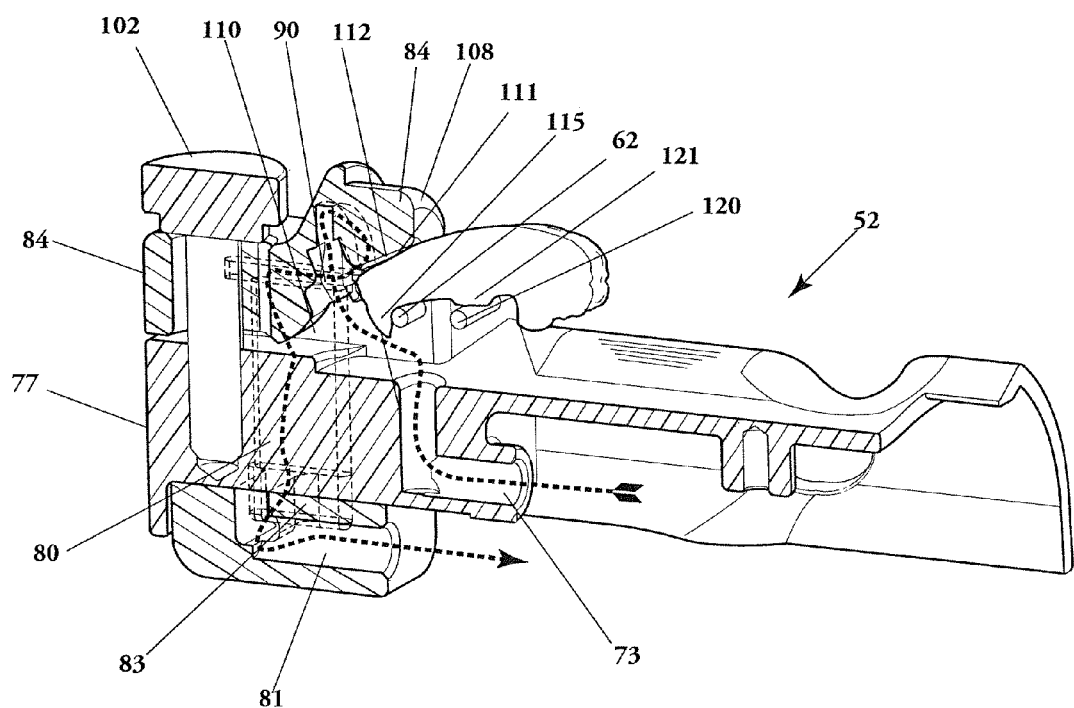
FIG. 17 is a partial view in axial section through the animal alignment system of FIG. 4.

As further seen in FIG. 6, the head and clamp member 84 is formed with a rearwardly-extending cantilevered clamping hood 108. Clamping hood 108 at least partially surrounds the fluid exhaust port 90 through which anesthesia gas may be exhausted. A small frustoconical or cup-shaped recess 110 immediately surrounds the fluid exhaust port 90 and transitions upwardly into a central arched recess 112 contoured to match the general contour of the bridge area of a rodent's nose 111 (FIGS. 9 and 17). Recess 112 is aligned and centered above and parallel with and symmetrical about the central channel 56 on the alignment bed 52, and tapers upwardly and rearwardly to provide a gradually-inclined inverted V-shaped arched wedging surface.

It can be appreciated that when the hood and clamp member 84 is axially forced rearwardly into contact with a rodent or similar specimen, the inverted V-shaped arched recess 112 engages the top and sides of a rodent's nose 111 (FIGS. 9 and 17) and presses or wedges the rodent's head downwardly and rearwardly into contact with the front transverse bite bar 62 over which a rodent's front teeth 115 are positioned. At the same time, the arched recess 112 laterally or transversely centers the rodent's head in axial symmetrical alignment over the central channel 56 by wedging the rodent's head within the inverted V-shaped recess or groove.

In this manner, the rodent's head is repeatably positioned both axially against the front bite bar 62 and transversely centered on the bite bar 62 over the central channel 56. The upwardly converging sidewalls 114 of the arched recess 112 effectively transversely wedge the rodent's head into a fixed predetermined position time after time for highly repeatable imagining.

Additional positioning accuracy can be obtained by providing a second registration surface in the form of a rear bite bar 120 (FIG. 3) behind and slightly above the first bite bar 62. For example, a stereotaxic upward and rearward angle of about 3 degrees from the horizontal plane of the alignment bed can be defined between the front and rear bite bars. The rear bite bar 120, like the front bite bar 62, is mounted on a pair of supports 122 spaced apart on opposite sides of the alignment bed 52. The rear bite bar 120 is positioned to engage and lock in position the rodent's rear upper molar teeth 121 (FIG. 17).

Because the bite bars 62 and 120 are located in a known orientation and position, and because they engage only hard bone or teeth of the rodent, it is possible to accurately and repeatably position a rodent on the alignment bed time and again. Moreover, the central groove 56 and the leg slots 58, 60 provide further longitudinal and transverse centering of the rodent's head and body on the alignment bed. As the bite bars can accommodate virtually any size rodent, the alignment bed can be used with rodents of varying sizes.

As further seen in FIG. 3, the alignment bed 52 can be formed with contoured recesses 126 for receiving monitors for monitoring the condition of a specimen. Recesses 126 can be formed as cylindrical pockets in the lower end of one or more of the front and rear leg channels 58, 60. By positioning a monitor, such as an ECG monitor, at the lower end of channels 58, 60, a rodent's hairless foot pads can be automatically positioned on the monitor. This arrangement also obviates the need for hairless or "nude" mice and rats, as well as the need to shave hairy or furry rodents. Pockets 126 insure the accurate and repeatable placement of a monitor on the sidewalls 61, as well as on a specimen.

An additional recess or pocket 128 can be formed along the central channel or groove 56 to receive and accurately and repeatably locate an additional monitor, such as a respiratory monitor or respiratory "pillow". Still another recess 132 can be formed along channel 56 adjacent the tail end of a specimen for receiving a pad 134 of absorbent material for absorbing liquid and solid waste from a specimen.

Again referring to FIG. 3, an optional nose, head or ear clamp 136 is shown provided on the head clamp 84. Clamp 136 can be formed with a pair of cantilevered resilient arms 138 configured to resiliently clamp or pinch opposite sides of a rodent's face or head. The arms 138 can be relatively small, as they need act only to center a rodent's head rather than clamp and fix a rodent's head by deep insertion into the rodent's ears.

A pair of hard plastic or rubber pads or nibs 140 can be provided on the ends of the arms 138 for positioning against the sides of a rodent's head or in a rodent's ears. The nibs 140 can be either fixed in position or transversely adjustable to conform to each specimen's head. In this manner, the clamp 84 acts as a yoke to provide additional axial alignment and centering of a rodent over channel 56, with arms 138 being spaced symmetrically laterally spaced over channel 56. The rounded pads or nibs 140 prevent damage to a rodent's ear which can otherwise occur with the use of conventional ear bars using set screws.

Figure 8:
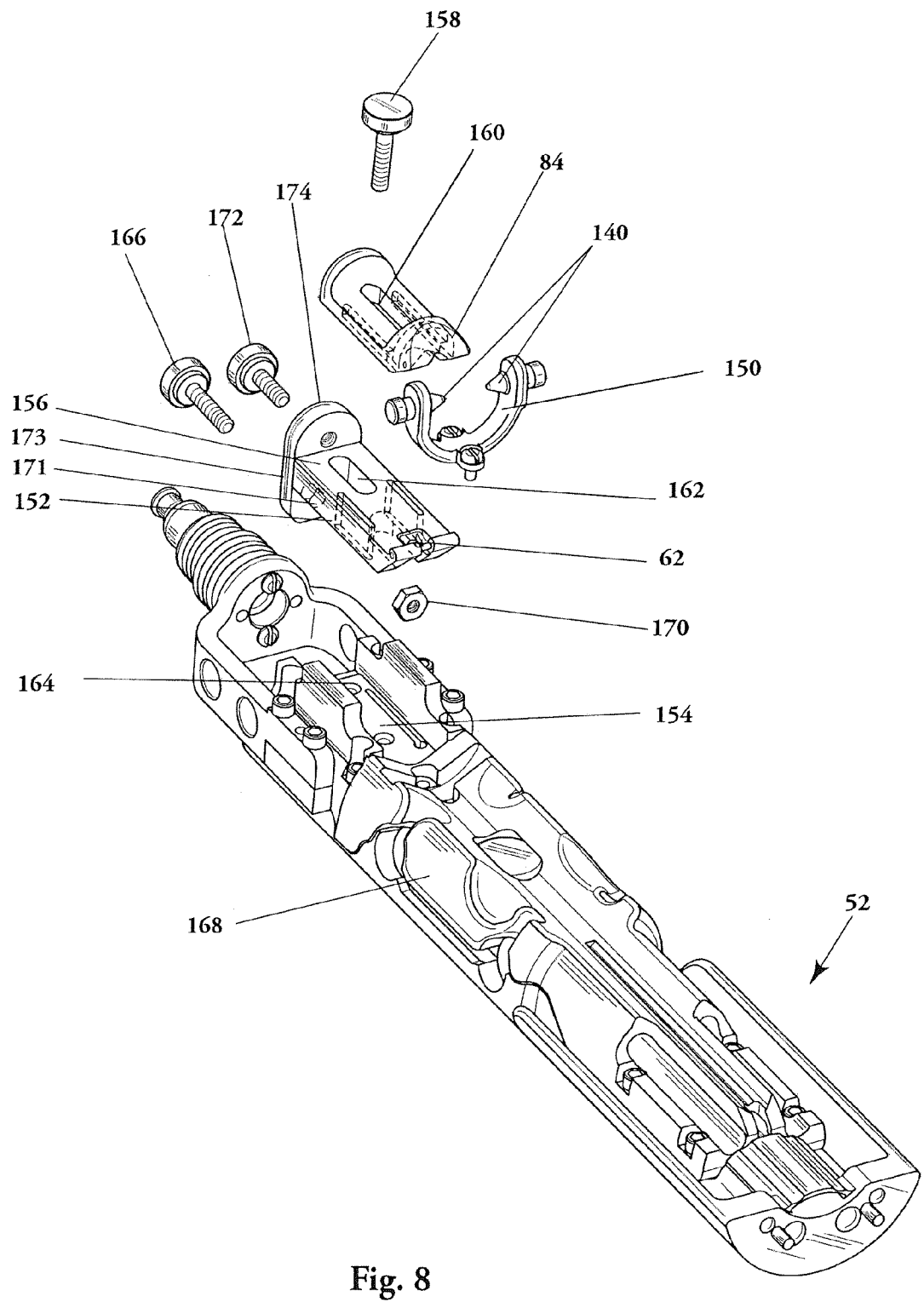
FIG. 8 is an exploded perspective view of another embodiment of alignment system and specimen holder having an adjustable bite bar and adjustable clamping assembly.

Another embodiment of a specimen head positioning system is shown in FIGS. 8 and 9 wherein a front incisor bite bar 62 is axially adjustable on the front end portion of the alignment bed 52, and an ear yoke 150 with ear cushions or nibs 140 is axially fixed in position on the alignment bed 52. An incisor slide 152 is closely slidably mounted in a slideway 154 molded or machined on the front end portion of the alignment bed 52.

A gas hood and clamp member 84 is slidably mounted on the top flat surface 156 of the incisor slide 152. The gas hood and clamp member 84 is held on the incisor slide 152 by an adjustable clamping screw 158 which passes through an elongated central slot 160 in the gas hood clamp member 84, through an elongated central slot 162 in the incisor slide 152 and into a threaded bore 164 in the slideway 154. Slots 160 and 162 are axially aligned, one over the other, for independent sliding movement of the gas hood and clamping member 84 and the incisor slide 152.

The incisor slide 152 can be accurately driven axially back and forth along the slideway 154 by a manual drive screw 166 threaded into an axially-extending bore in the end face 168 of the alignment bed 52. A retainer nut 170 is fixed on the drive screw 166 to provide an abutment surface for retracting the incisor slide 152 away from a specimen. A non-threaded clearance bore 171 is formed through a flange 173 on the incisor slide for free passage of the drive screw 166.

The gas hood and clamping member 84 is also axially adjustable with a drive screw 172 which is threaded through flange 174 on the incisor slide 152. In use, an operator places a specimen, such as a laboratory rodent, in the yoke 150 and then hooks the specimen's incisors over the front bite bar 62 (a rear molar bite bar may also be provided on the incisor slide). The operator then retracts the incisor slide with drive screw 166 to place the specimen's incisors under a light tension or pull. The gas hood and clamp 84 is then driven into clamping engagement with the specimen's nose by turning drive screw 172. At this point, the clamping screw 158 is tightened to firmly hold the gas hood and clamping member 84 and the incisor slide 152 in an accurate axially-fixed location. At this point, the specimen is secure for imaging.

Figure 10:
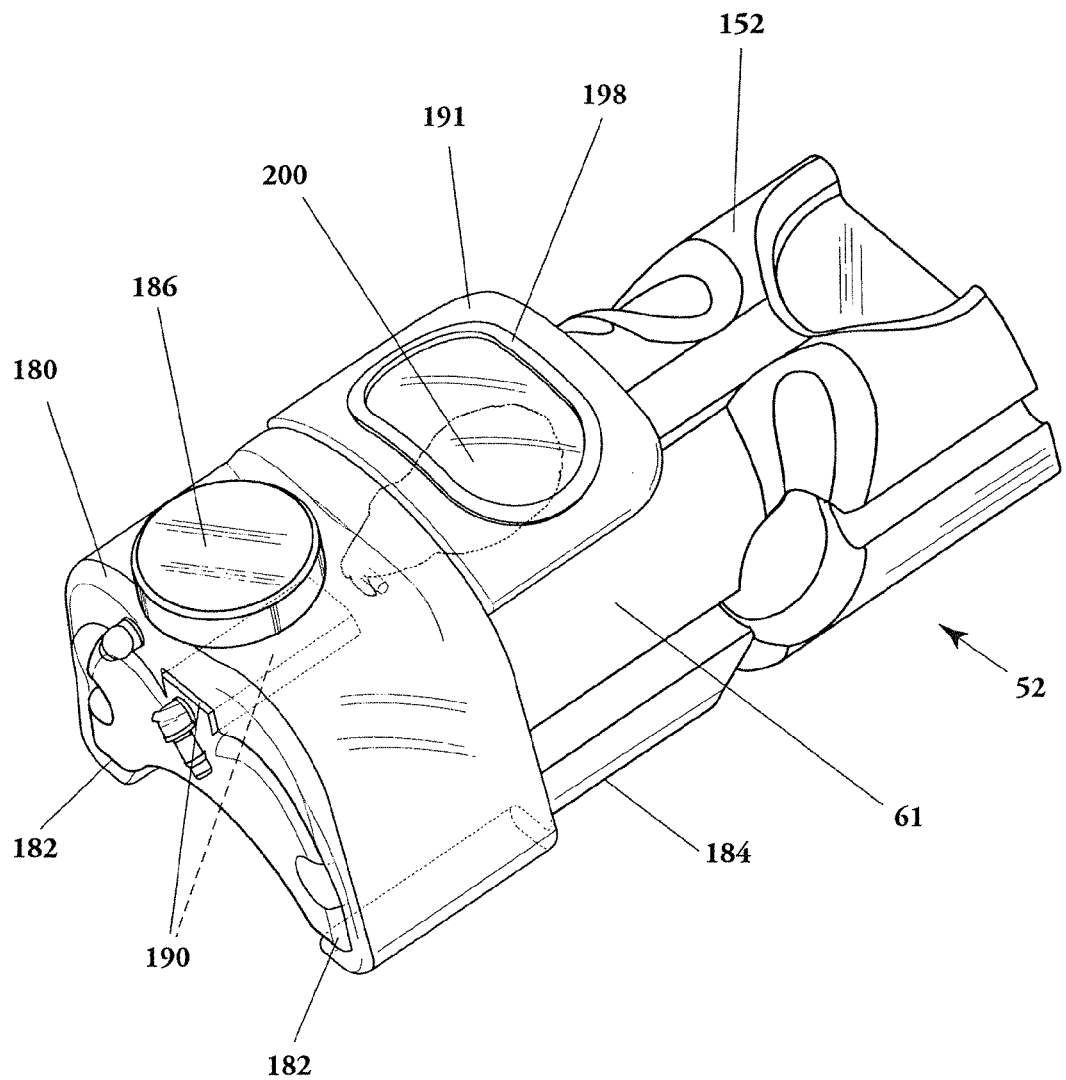
FIG. 10 is a partial perspective view of a surface coil positioning assembly mounted on a representative specimen alignment bed.
Figure 11:
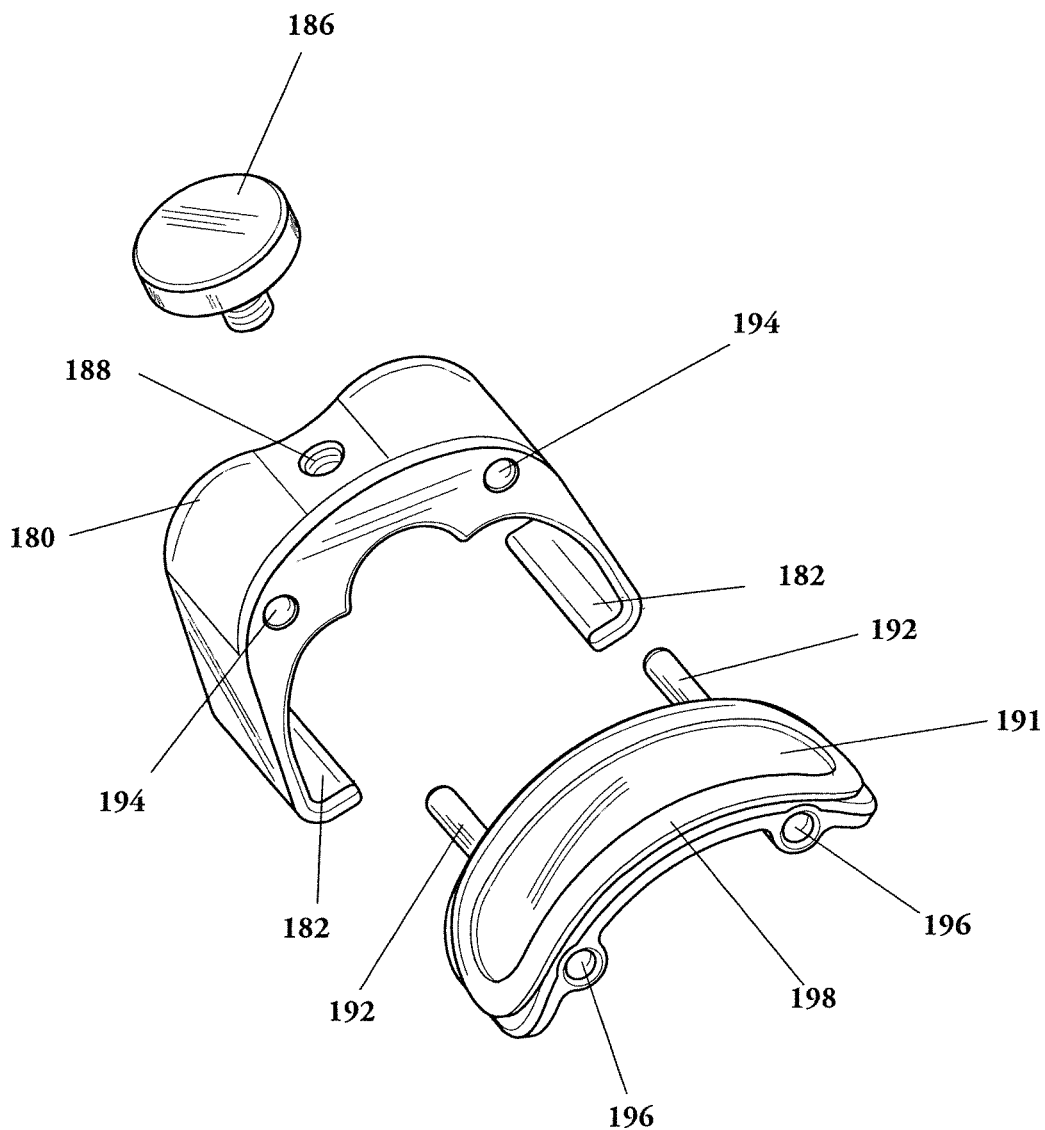
FIG. 11 is an exploded perspective view of the surface coil positioning assembly of FIG. 10.
Figure 12:
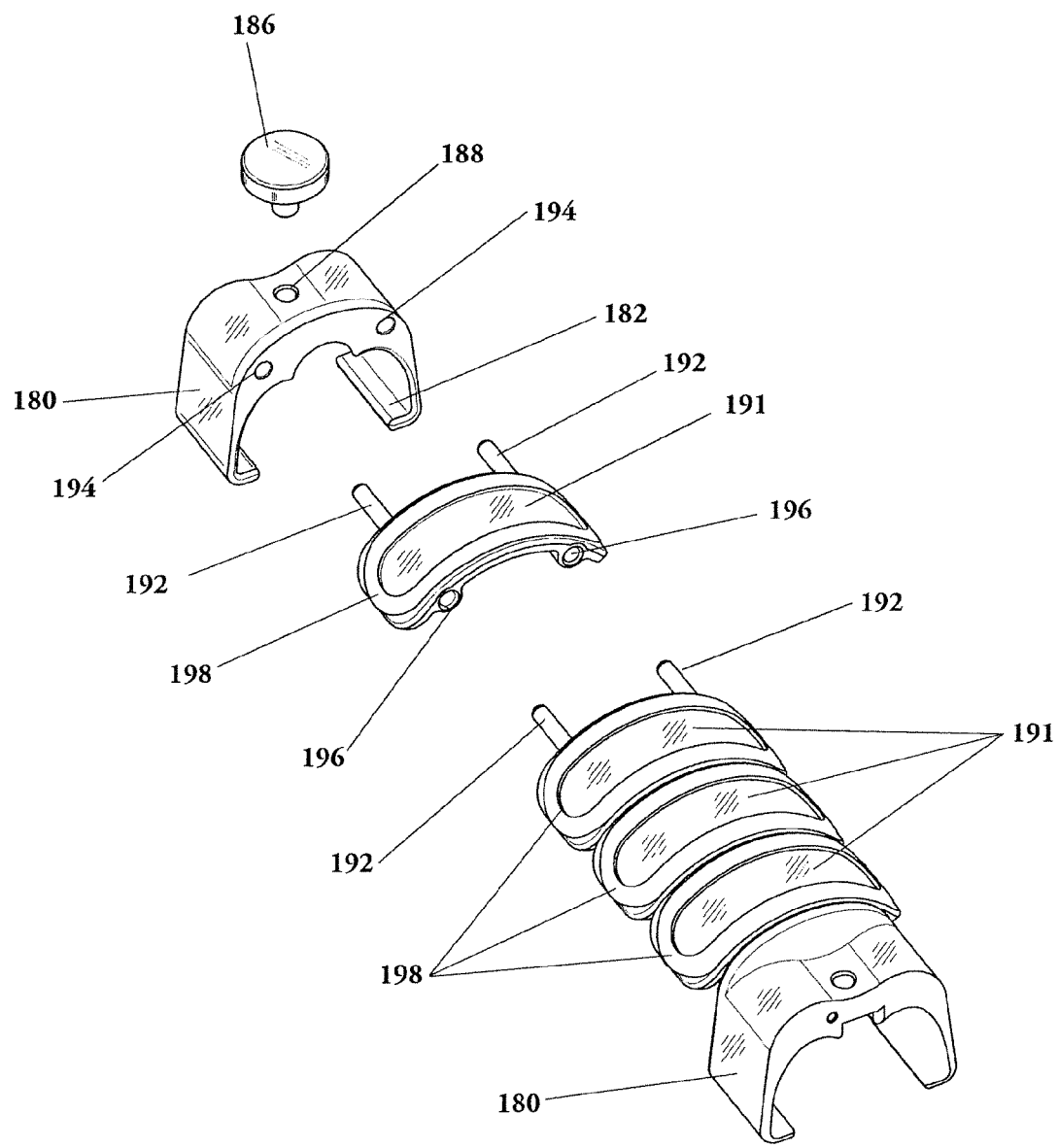
FIG. 12 is an exploded perspective view of a modular coil positioning assembly allowing serial interconnection of a set of surface coils.

Another embodiment of the specimen support system is shown in FIGS. 10, 11 and 12 wherein an easily mountable and easily demountable plastic coil holder 180 is formed with a pair of inwardly-projecting clamping rails 182 for clamping against the undersurface 184 of the sidewalls 61 of the alignment bed 52. A clamp screw or set screw 186 is threaded through a threaded bore 188 in a flattened central portion of the roof of the coil holder 180. By tightening the set screw 186, the tip of the set screw engages a pad 190 on the top of the front end portion of the alignment bed 52 and lifts the coil holder 180 upwardly. This causes the clamping rails 182 to engage the undersurface 184 of the alignment bed side walls 61 and thereby fix the coil holder 180 in a desired fixed axial location on the alignment bed 52.

By loosening the set screw 186, the coil holder 180 can be easily mounted on and/or slid back and forth along the alignment bed and then fixed in axial position by tightening the set screw 186 or removed from the alignment bed, as desired. This slidable mounting arrangement is very quick and simple.

A surface coil support platform 191 includes a pair of mounting pins 192 which are dimensioned to fit closely within smooth axial bores 194 formed in the roof of the coil holder 180. As seen in FIG. 12, each coil support platform 191 can be formed with axial bores 196 to receive the mounting pins 192 on additional coil support platforms 191. In this manner, any number of surface coil platforms 191 can be interconnected as desired for enhancing the imaging resolution of the specimen image. As further seen in FIG. 12, more than one coil holder can be clamped to the alignment bed for holding additional support platforms 191.

One or more surface coils 198 is mounted on each coil support platform 191 in the form of, for example, a loop of copper, gold or other nonmagnetic material. The surface coils 198 can be plated onto the platforms 190, insert molded, or adhesively bonded to the coil platforms 191 using techniques common to circuit board manufacture.

The coil support platforms 191 and the coil holders 180 can be formed of clear molded rigid plastic. This allows an operator of an imaging machine to see through the coil holders and coil support platforms and to view and monitor the condition, position and location of a specimen 200 (FIG. 13) clamped in position on the alignment bed 52. This surface coil mounting arrangement also allows an operator to locate the surface coils 198 very close to the specimen 200 to achieve the best imaging resolution.

Figure 13:
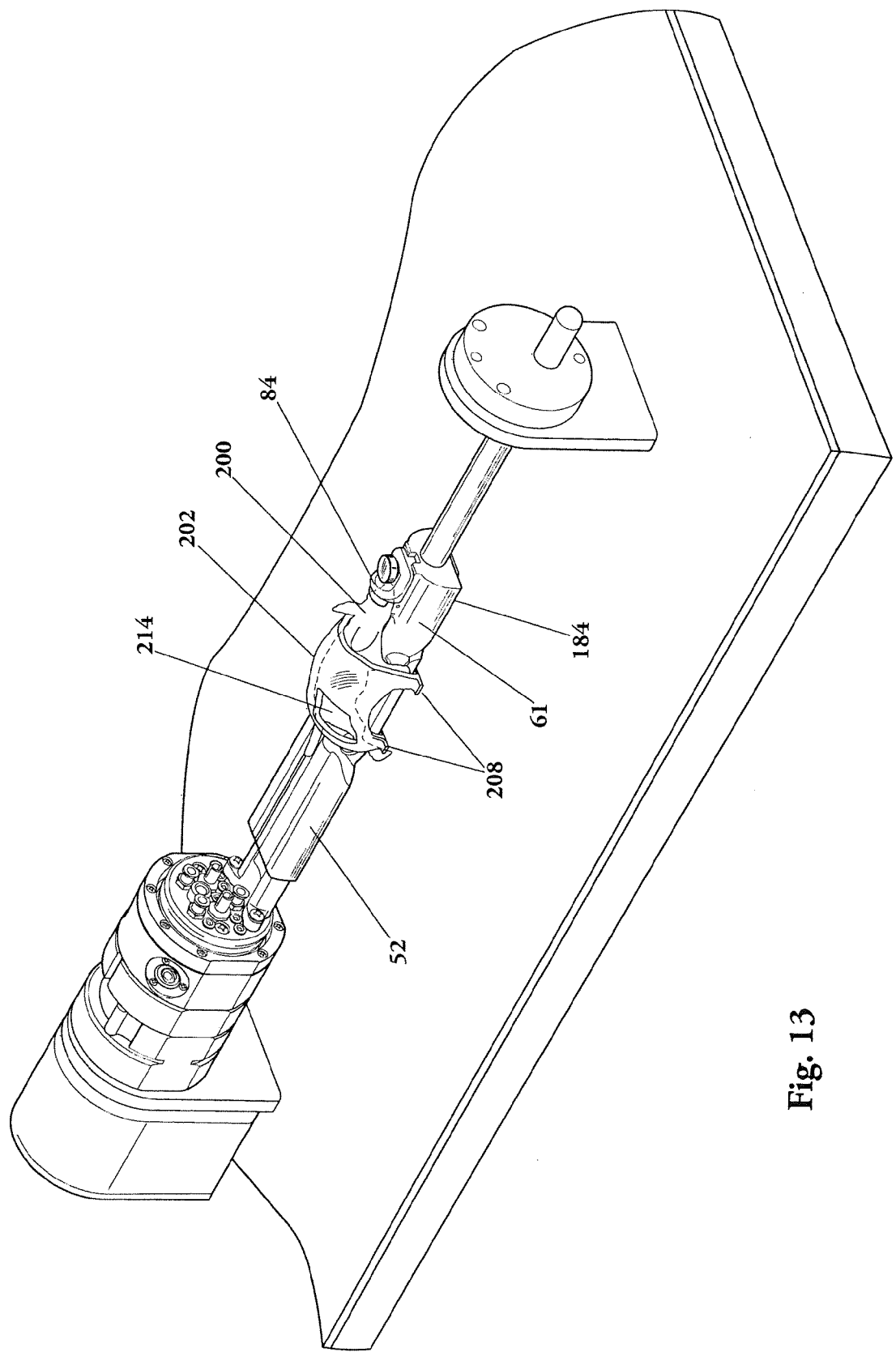
FIG. 13 is a perspective view of a laboratory specimen held in position with a combination surface coil and specimen retainer clamped to a representative specimen alignment system.
Figure 14:
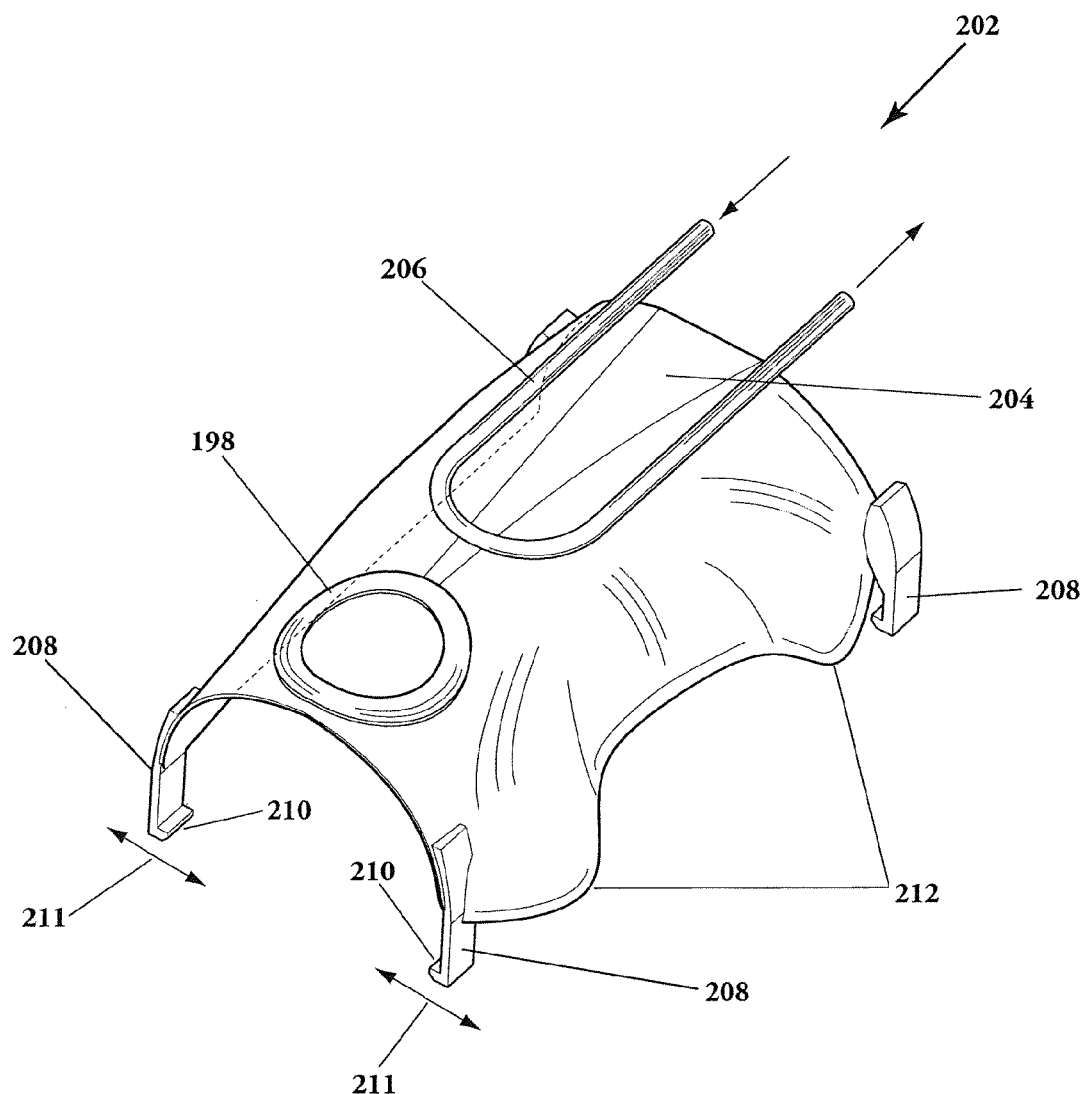
FIG. 14 is a perspective view of a combination surface coil and specimen retainer similar to that of FIG. 13 and including a specimen warming conduit.

Another multipurpose coil support platform and specimen retainer 202 is shown in FIGS. 13 and 14. In this embodiment, one or more surface coils 198 is provided on an arched support surface 204 in a manner as described above. A fluid conduit 206 can be provided on the specimen retainer 202 as a molded channel or as a separate component such as a plastic tube bonded to the retainer 202. Warm air, water or other fluid can be pumped and recirculated through the fluid conduit 206 to warm the specimen 200 when it is positioned in a cold bore of a supercooled superconducting imaging magnet.

Retainer 202 can be mounted to the specimen alignment bed 52 with a resilient snap-fit connection provided by cantilevered spring legs 208. Legs 208 include hooked free end portions 210 which deflect transversely outwardly when pushed down on top of the sidewalls 61 of the alignment bed 52 and then snap back into spring-biased engagement against the sidewalls 61 and sidewall undersurface 184 as shown by directional arrows 211.

Retainer 202 also serves as a specimen retainer to gently clamp a specimen 200 in a predetermined position on the alignment bed 52. The shape of the inner surface of the retainer 202 is contoured to match the general contours of the body of a specimen so that when the retainer engages the back and sides of a specimen, it closely fits against the specimen without any high pressure points or pinch points. This close intimate contact helps to transfer heat from the warming fluid to the specimen 200.

Further support and positioning can be provided to the specimen 200 by forming outwardly contoured recesses or cut-out portions 212 in the support surface 204 to match the position of the specimen's front and rear feet located in the front and rear leg channels 60, 58 formed in the alignment bed 52.

An additional cut-out or window 214 can be provided in the support surface 204 for allowing the specimen to be injected through the window 214. The position of coil 198 can be fixed to lie over any chosen portion of the specimen.

Figure 15:
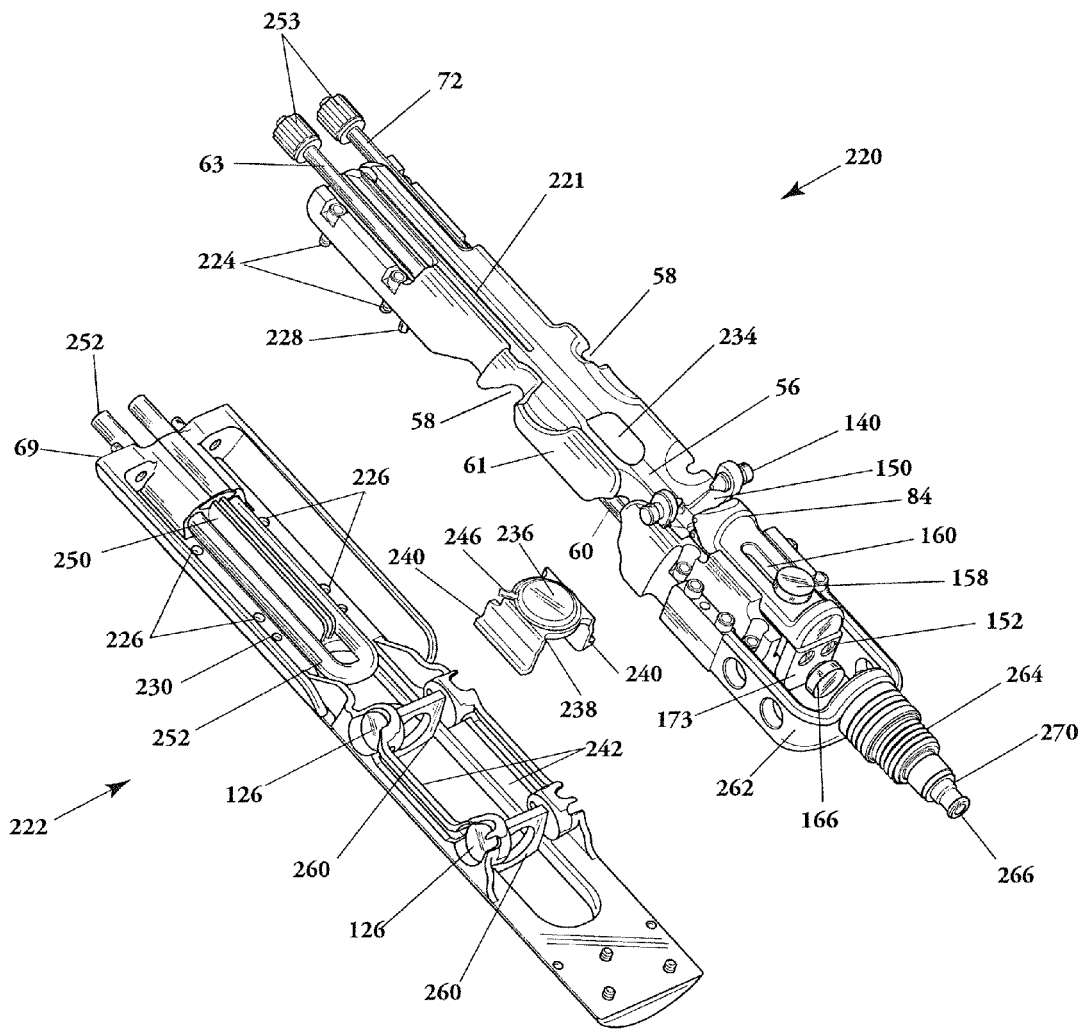
FIG. 15 is an exploded perspective view of a specimen alignment system having an upper specimen holding platform and a lower instrumentation holding platform.
Figure 16:
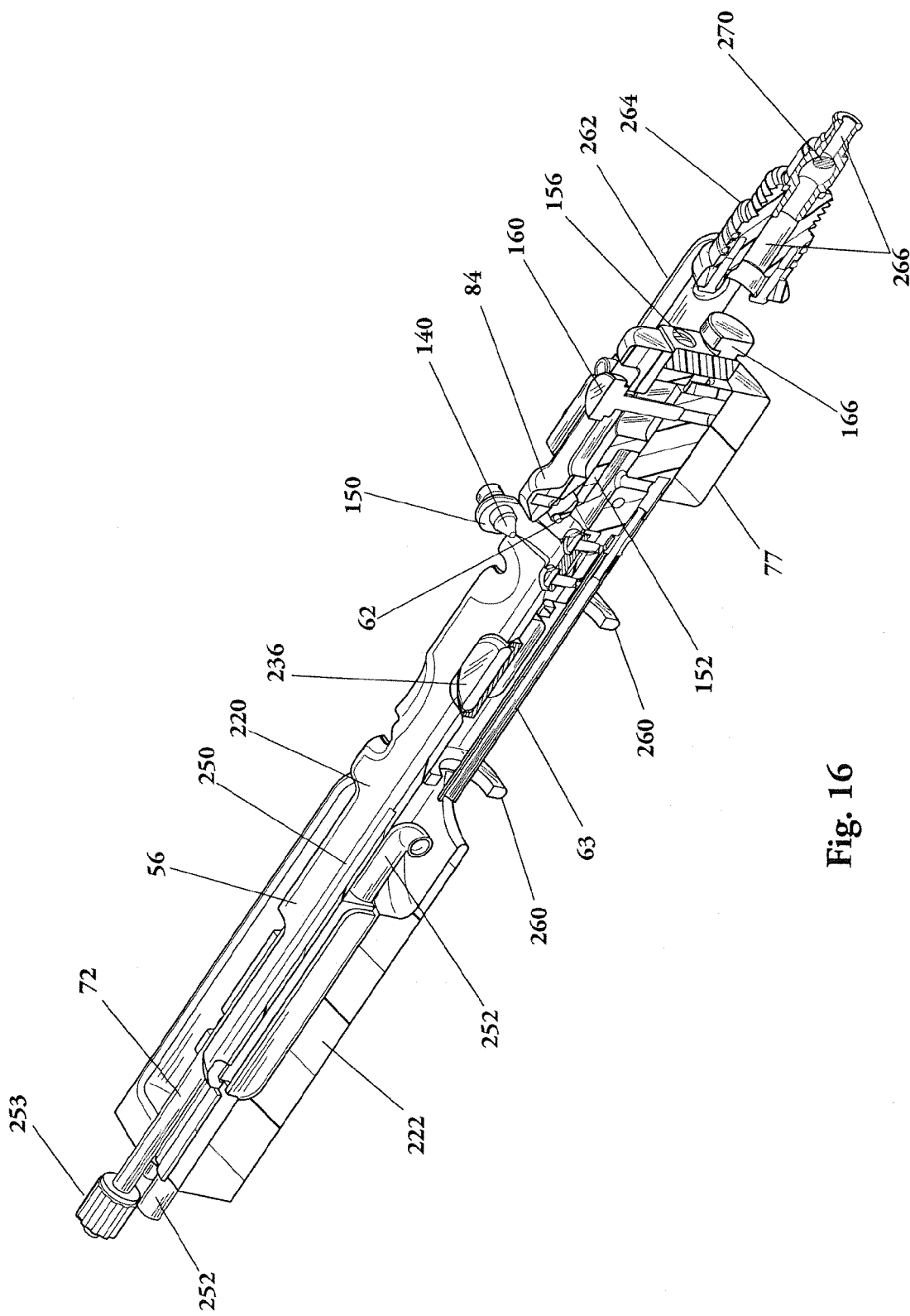
FIG. 16 is a view in axial section through the specimen alignment system of FIG. 15.

Another embodiment of the specimen alignment system is shown in FIGS. 15 and 16. In this example, the alignment bed is constructed with an upper specimen alignment bed or animal platform 220 and a lower instrumentation support platform 222. The upper platform 220 can be releasably secured to the lower platform 222 by plastic screws 224 engaged in threaded bores 226. Alignment pins 228 and sockets 230 can provide further alignment and registration between the animal platform 220 and the instrumentation platform 222.

An advantage to this construction is that an animal specimen 200 (FIG. 13)*can* be secured to the upper platform 220 as described above without connecting any instrumentation to the animal. As all the instrumentation, sensors, electronics and most or all of the fluid flow tubes can be provided on the lower instrumentation support platform, animal specimens can be quickly and easily secured to the animal platform either before or after the animal platform 220 is secured to the instrumentation support platform 222.

The animal platform 220 includes a central longitudinal axially-extending trough or body alignment groove 56 and a tail alignment groove 221. First and second rear leg slots, grooves or channels 58 receive and position the rear legs of a specimen and first and second front leg slots, grooves or channels 60 receive and position the front legs of a specimen on the animal platform 220.

A central longitudinally-elongated aperture or clearance hole 234 is formed through the alignment groove 56 between the front and rear leg channels 60, 58 and aligned with a specimen's chest and lungs. Aperture 234 allows for the free passage of a respiratory sensor or "pillow" 236 mounted on the lower instrumentation support platform 222. An axially-slidable pedestal 238 has rails 240 which slide along slideway ledges 242 on the lower instrumentation support platform 222 to accurately adjust and axially align the respiratory sensor 236 with a specimen's lungs.

Additional monitors or sensors can be mounted on the instrumentation support platform 222 in sensor pockets or sensor holders 126 which are positioned to engage a specimen's feet, as described above. Electrical leads from the sensors mounted in the sensor holders 126 along with the fluid tube 246 on the respiratory sensor 236 are guided to the end wall 69 of the support platform 222 by a longitudinally grooved central axial wall 250.

Warming fluid can be introduced and recirculated between the animal platform 220 and the instrumentation platform 222 by a flow tube 252 which runs axially between the platforms in a closed loop. Anesthesia gas is delivered to the specimen through gas delivery flow tube 63 and exhausted through gas exhaust flow tube 72 as described above. The flow tubes 63 and 72 are routed through apertured bulkheads 260 on the lower support platform 222, and communicate with one or more ported gas flow blocks 77 as described above. Fluid quick-connect couplings 253 can be provided on the flow tubes for easy connection and disconnection to panel 34.

A U-shaped plastic spacer band 262 is mounted to the front end of the animal support platform 220. A hollow radially-stepped threaded connector 264 is fixed to the space band 262 for threaded connection to an end cap 48 on a specimen tube 39 (FIG. 1) for fixing the specimen tube against the panel 34 and for providing support to the inner end of the specimen alignment system. A central passage 266 extends through the connector 264 for passage of a hypodermic needle. A check valve 270 is provided in passage 266 to allow for passage of fluids via a syringe but to prevent escape of gas from cylinder tube 39.

The upper animal platform 220 includes a combination exhaust hood and head clamp 84 which is manually slidable over an incisor bite bar slide 152 which can be axially adjusted as described above. The use and operation of this specimen alignment system is substantially similar to that of the prior disclosed embodiments.

There has been disclosed heretofore the best embodiment of the invention presently contemplated. However, it is to be understood that various changes and modifications may be made thereto without departing from the spirit of the invention.

What is claimed is:

1. A specimen support, comprising:
 a longitudinally-extending elongated bed having a front portion, a rear portion, a top portion and a bottom portion;
 a head clamp, adjustable about said front portion of said bed for engaging a specimen's head, said head clamp comprising an exhaust passage;

a ported block provided on said front portion of said bed below said head clamp, said ported block comprising:
an intake port defining a gas flowpath from said bottom portion to said top portion of said bed wherein said intake port is in fluid communication with said head clamp exhaust passage, and
an exhaust port defining a gas flowpath from said head clamp exhaust passage at said top portion of said bed to said bottom portion of said bed;
wherein said head clamp is movable on said front portion of said bed for aligning said head clamp exhaust passage with said intake port and said exhaust port;
a gas delivery line extending from said rear portion of said bed to said intake port; and
a gas exhaust line extending from said exhaust port to said rear portion of said bed.

2. The support of claim 1, wherein said head clamp further comprises a gas port fluidly communicating with said ported block.

3. The support of claim 1, wherein said gas flowpath comprises first and second anesthesia gas exhaust ports.

4. The support of claim 1, further comprising at least one bite bar coupled to said front portion of said bed and wherein said gas flowpath is located adjacent to said bite bar.

5. The support of claim 1, wherein said ported block comprises a ported manifold block.

6. A specimen support for holding a specimen during an imaging procedure, comprising:
a specimen alignment bed having a front portion, a rear portion a top portion and a bottom portion;
a specimen head holder movably engaged with said front portion of said specimen alignment bed, said head holder comprising an exhaust passage formed therethrough;
an anesthesia gas delivery line extending from said rear portion of said specimen alignment bed to said front portion of said specimen alignment bed for delivering anesthesia gas to a specimen and wherein said anesthesia gas delivery line extends upwardly through said specimen alignment bed from said bottom portion to said top portion of said bed adjacent to said specimen head holder;
an anesthesia gas exhaust line extending from said front portion of said specimen alignment bed to said rear portion of said specimen alignment bed for exhausting anesthesia gas from said front portion of said specimen alignment bed;
an intake port on said front portion of said specimen alignment bed for delivering anesthesia gas from said gas delivery line to a specimen; and
an exhaust port on said front portion of said specimen alignment bed for exhausting anesthesia gas from said gas delivery line away from said front portion of said specimen alignment bed
wherein said head holder exhaust passage is movably aligned with said intake port and said exhaust port for providing fluid communication between said gas delivery line and said gas exhaust line.

7. The specimen support of claim 6, wherein said intake port is disposed adjacent to said specimen head holder.

8. The specimen support of claim 6, wherein said exhaust port is disposed adjacent to said head holder.

9. The specimen support of claim 6, wherein said anesthesia gas exhaust line extends downwardly from said specimen head holder.

10. The specimen support of claim 6, wherein said anesthesia gas exhaust line extends through a portion of said specimen head holder.

11. The specimen support of claim 6, further comprising a ported block portion provided on said front portion of said specimen alignment bed and wherein said anesthesia gas delivery line is fluidly connected to said ported block portion.

12. The specimen support of claim 11, wherein said intake port is on said ported block portion.

13. The specimen support of claim 6, further comprising a ported exhaust manifold block provided on said front portion of said specimen alignment bed, and wherein said anesthesia gas exhaust line is fluidly connected to said ported exhaust manifold block.

14. The specimen support of claim 6, wherein said exhaust port is on said specimen head holder.

15. The specimen support of claim 6, further comprising a pair of distribution exhaust channels fluidly communicating with said exhaust port.

16. The specimen support of claim 15, further comprising an exhaust collection chamber for receiving anesthesia gas exhausted through said exhaust port.

17. The specimen support of claim 6, wherein said specimen head holder is axially adjustable on said specimen alignment bed.

18. The specimen support of claim 6, further comprising an exhaust hood provided on said specimen head holder for directing anesthesia gas through said intake port.

19. The specimen support of claim 6, wherein said anesthesia gas delivery line and said anesthesia gas exhaust line are located one above the other.

* * * * *